(12) United States Patent
Cannell et al.

(10) Patent No.: US 12,351,546 B2
(45) Date of Patent: Jul. 8, 2025

(54) METHOD OF MITIGATING CONVERSION OF VOLATILE TERPENE SPECIES

(71) Applicant: Givaudan SA, Vernier (CH)

(72) Inventors: Jonathon Cannell, Cincinnati, OH (US); Andrew Finn, Milford, OH (US); Chad Allen Hansen, Lebanon, OH (US); Geoff Marshall-Hill, Newport Pagnell (GB)

(73) Assignee: Givaudan SA, Vernier (CH)

( * ) Notice: Subject to any disclaimer, the term of this patent is extended or adjusted under 35 U.S.C. 154(b) by 169 days.

(21) Appl. No.: 18/032,037

(22) PCT Filed: Oct. 29, 2021

(86) PCT No.: PCT/EP2021/080119
§ 371 (c)(1),
(2) Date: Apr. 14, 2023

(87) PCT Pub. No.: WO2022/090464
PCT Pub. Date: May 5, 2022

(65) Prior Publication Data
US 2024/0018077 A1    Jan. 18, 2024

Related U.S. Application Data

(60) Provisional application No. 63/174,359, filed on Apr. 13, 2021, provisional application No. 63/107,841, filed on Oct. 30, 2020.

(51) Int. Cl.
*C07C 29/80* (2006.01)
*A23L 27/20* (2016.01)
*C07C 29/88* (2006.01)

(52) U.S. Cl.
CPC ............ *C07C 29/80* (2013.01); *A23L 27/203* (2016.08); *C07C 29/88* (2013.01)

(58) Field of Classification Search
CPC ......... C07C 29/80; C07C 29/94; C07C 29/88; A23L 27/203
See application file for complete search history.

(56) References Cited

U.S. PATENT DOCUMENTS

| | | | | |
|---|---|---|---|---|
| 5,847,226 A | * | 12/1998 | Muller | ................ C07C 29/50 568/349 |
| 2003/0017216 A1 | * | 1/2003 | Schmidt | ............... A61K 36/185 424/725 |

FOREIGN PATENT DOCUMENTS

| JP | 2004 067723 A | 3/2004 |
|---|---|---|
| WO | 02/50053 A2 | 6/2002 |
| WO | 2016/029153 A1 | 2/2016 |
| WO | 2016/029187 A2 | 2/2016 |

OTHER PUBLICATIONS

International Search Report for Application No. PCT/EP2021/080119, mailed on Feb. 16, 2022.
International Written Opinion for Application No. PCT/EP2021/080119, mailed on Feb. 16, 2022.

* cited by examiner

*Primary Examiner* — Renee Robinson
(74) *Attorney, Agent, or Firm* — Curatolo Sidoti & Trillis Co., L.P.A.; Salvatore A. Sidoti; Floyd Trillis, III

(57) ABSTRACT

The conversion of nootkatol to nootkatene in a terpene blend is mitigated or prevented by substantially or completely separating the nootkatols such as α-nootkatol from compounds present in the terpene blend that catalyze the chemical reaction of nootkatol to nootkatene, and/or by at least partially neutralizing the compounds present in the terpene blend that catalyze the chemical reaction of nootkatol to nootkatene. Methods of preparing terpene blends, terpene blends, flavour compositions containing the terpene blends, beverages and foodstuffs containing the flavour compositions, fragrance compositions containing the terpene blends, and fragranced products containing the fragrance composition are also disclosed.

9 Claims, No Drawings

METHOD OF MITIGATING CONVERSION OF VOLATILE TERPENE SPECIES

CROSS REFERENCE TO RELATED APPLICATIONS

This application is a national stage application of International Application No. PCT/EP2021/080119, filed 29 Oct. 2021, which claims priority from U.S. Provisional Patent Application Nos. 63/107,841, filed on 30 Oct. 2020 and 63/174,359, filed 13 Apr. 2021, all of which applications are incorporated herein by reference.

TECHNICAL FIELD

The present disclosure relates to mitigating the conversion of volatile terpenes into undesired compounds. The present disclosure more particularly relates to methods for mitigating or preventing the conversion of nootkatols to nootkatene, methods of making terpene blends, terpene blends, and beverage, foodstuffs and fragrance products containing the terpene blends.

BACKGROUND

Nootkatone is a volatile essential oil blend that is derived from grapefruit and Alaska yellow cedar trees. Nootkatone oil blends are commonly used as citrus flavouring agents for food and beverages and as fragrance ingredients. With respect to food and beverage products, the α-nootkatol molecule is widely recognized as a key component in nootkatone oil blends, as the α-nootkatol contributes to the acceptable organoleptic profile of nootkatone oil blends.

The raw material terpene blends containing nootkatol may also contain fatty acids and other high boiling point impurities that catalyze the reaction of nootkatol to nootkatene. Fractional distillation must be carried out on a raw material terpene blend containing nootkatol to prepare a final commercial nootkatone oil blend suitable for sale to customers. During the fractional distillation process the raw material terpene blend containing the nootkatol is heated at elevated temperatures for a sustained period of time. The elevated temperatures trigger fatty acids and other high boiling point impurities present in the raw material terpene blend to catalyze the undesired reaction of nootkatol to nootkatene. This results in a decrease of the level of nootkatol and an increase of the level of nootkatene present in the terpene blend. The reduced nootkatol levels or increased nootkatene levels result in changes to the taste profile of a nootkatone oil blend, such that a nootkatone oil blend with these altered taste profile characteristics will not meet current market expectations.

The nootkatene that forms continuously during a batch fractional distillation process will contaminate the distillate fractions throughout the distillation and will prevent the creation of high quality terpene blends. Terpene blends demanded in the market contain little or no nootkatene. The presence of nootkatene above a certain level in a terpene blend will impact the organoleptic properties, customer satisfaction and may be rejected by the customer based on analytical specifications.

As certain nootkatone oil blends include fatty acids and other high boiling point impurities that catalyze the undesired reaction of nootkatol to nootkatene, there is a need in the art to develop a method for processing raw material nootkatone oil blends that maintains desired α-nootkatol content while minimizing the formation of nootkatene.

SUMMARY

According to certain illustrative embodiments, provided is a method of mitigating or preventing the conversion of nootkatol to nootkatene comprising providing a feed containing at least one nootkatol and at least one compound that catalyzes the conversion of nootkatol to nootkatene and, either (i) separating at least a portion of the nootkatol from the at least one compound that catalyzes the conversion of nootkatol to nootkatene, or (ii) neutralizing at least a portion of the at least one compound that catalyzes the conversion of nootkatol to nootkatene.

According to certain illustrative embodiments, provided is a method of mitigating or preventing the conversion of nootkatol to nootkatene comprising providing a feed containing nootkatol and at least one compound that catalyzes the conversion of nootkatol to nootkatene and, separating at least a portion of the nootkatol from the at least one compound that catalyzes the conversion of nootkatol to nootkatene.

According to certain illustrative embodiments, provided is a method of mitigating or preventing the conversion of nootkatol to nootkatene comprising providing a feed containing nootkatol and at least one compound that catalyzes the conversion of nootkatol to nootkatene, and neutralizing at least a portion of the at least one compound that catalyzes the conversion of nootkatol to nootkatene.

According to certain illustrative embodiments, also provided is a method of preparing a terpene blend comprising providing a feed containing nootkatol and at least one compound that catalyzes the conversion of nootkatol to nootkatene, treating the feed to mitigate or prevent conversion of nootkatol to nootkatene, and carrying out fractional distillation on the second feed containing the nootkatol.

According to certain illustrative embodiments, the method of preparing a terpene blend comprises providing a feed containing nootkatol and at least one compound that catalyzes the conversion of nootkatol to nootkatene, treating the feed to mitigate or prevent conversion of nootkatol to nootkatene by either (i) separating at least a portion of the nootkatol from the at least one compound that catalyzes the conversion of nootkatol to nootkatene to create a second feed containing the nootkatol, or (ii) neutralizing at least a portion of the at least one compound that catalyzes the conversion of nootkatol to nootkatene, and carrying out fractional distillation on the feed or the second feed.

According to certain illustrative embodiments, the method of preparing a terpene blend comprises providing a feed containing nootkatol and at least one compound that catalyzes the conversion of nootkatol to nootkatene, treating the feed to mitigate or prevent conversion of nootkatol to nootkatene by separating at least a portion of the nootkatol from the at least one compound that catalyzes the conversion of nootkatol to nootkatene to create a second feed containing the nootkatol, and carrying out fractional distillation on the second feed containing the nootkatol.

According to certain illustrative embodiments, the method of preparing a terpene blend comprises providing a feed containing nootkatol and at least one compound that catalyzes the conversion of nootkatol to nootkatene, treating the feed to mitigate or prevent conversion by neutralizing at least a portion of the compounds present in the feed that catalyze the conversion of nootkatol to nootkatene, and carrying out fractional distillation on the treated feed.

According to certain embodiments, provided is a terpene blend prepared in accordance with the method comprising providing a feed containing nootkatol and at least one compound that catalyzes the conversion of nootkatol to nootkatene, treating the feed to mitigate or prevent conversion of nootkatol to nootkatene by either (i) separating at least a portion of the nootkatol from the at least one compound that catalyzes the conversion of nootkatol to nootkatene to create a second feed containing the nootkatol, or (ii) neutralizing at least a portion of the at least one compound that catalyzes the conversion of nootkatol to nootkatene, and carrying out fractional distillation on the feed or the second feed.

According to certain embodiments, the terpene blend is prepared in accordance with the method comprising providing a feed containing nootkatol and at least one compound that catalyzes the conversion of nootkatol to nootkatene, treating the feed to mitigate or prevent conversion of nootkatol to nootkatene by separating at least a portion of the nootkatol from the at least one compound that catalyzes the conversion of nootkatol to nootkatene to create a second feed containing the nootkatol, and carrying out fractional distillation on the second feed.

According to certain illustrative embodiments, the terpene blend is prepared in accordance with the method comprising providing a feed containing nootkatol and at least one compound that catalyzes the conversion of nootkatol to nootkatene, treating the feed to mitigate or prevent conversion by neutralizing at least a portion of the compounds present in the feed that catalyze the conversion of nootkatol to nootkatene, and carrying out fractional distillation on the treated feed.

According to certain illustrative embodiments, provided is a beverage or foodstuff comprising a beverage or foodstuff base and a terpene blend prepared by treating a feed containing nootkatol and at least one compound that catalyzes the conversion of nootkatol to nootkatene to mitigate or prevent conversion of nootkatol to nootkatene, and carrying out fractional distillation on the feed.

According to certain illustrative embodiments, the beverage or foodstuff comprises a beverage or foodstuff base and a terpene blend prepared by treating a feed containing nootkatol and at least one compound that catalyzes the conversion of nootkatol to nootkatene to mitigate or prevent conversion of nootkatol to nootkatene by separating at least a portion of the nootkatol from the compounds in the feed that catalyze the conversion of nootkatol to nootkatene to create a second feed containing the nootkatol, and carrying out fractional distillation on the second feed.

According to certain illustrative embodiments, the beverage or foodstuff comprises a beverage or foodstuff base and a terpene blend prepared by providing a feed containing nootkatol and at least one compound that catalyzes the conversion of nootkatol to nootkatene, treating the feed to mitigate or prevent conversion by neutralizing at least a portion of the compounds present in the feed that catalyze the conversion of nootkatol to nootkatene, and carrying out fractional distillation on the treated feed.

Also disclosed is a flavour composition comprising the terpene blend prepared in accordance with the presently disclosed methods and a flavour base.

Also disclosed is a food or beverage product comprising the terpene blend prepared in accordance with the presently disclosed methods or a flavour composition comprising the terpene blend and a flavour product base.

Also disclosed is a method of preparing a food or beverage product comprising mixing together the terpene blend prepared in accordance with the presently disclosed methods, or a flavour composition comprising the terpene blend, with a food or beverage product base.

According to certain illustrative embodiments, a fragrance product comprising a fragrance product base and a terpene blend prepared by treating a feed containing nootkatol and at least one compound that catalyzes the conversion of nootkatol to nootkatene to mitigate or prevent conversion of nootkatol to nootkatene, and carrying out fractional distillation on the treated feed.

According to certain illustrative embodiments, the fragrance product comprises a fragrance product base and a terpene blend prepared by treating a feed containing nootkatol and at least one compound that catalyzes the conversion of nootkatol to nootkatene to mitigate or prevent conversion of nootkatol to nootkatene by separating at least a portion the nootkatol from the catalyst compounds in the feed that catalyze the conversion of nootkatol to nootkatene to create a second feed containing the nootkatol, and carrying out fractional distillation on the second feed.

According to certain illustrative embodiments, the fragrance product comprises a fragrance product base and a terpene blend prepared by providing a feed containing nootkatol and at least one compound that catalyzes the conversion of nootkatol to nootkatene, treating the feed to mitigate or prevent conversion by neutralizing at least a portion of the compounds present in the feed that catalyze the conversion of nootkatol to nootkatene, and carrying out fractional distillation on the treated feed.

Also disclosed is a fragrance composition comprising the terpene blend prepared in accordance with the presently disclosed methods and a fragrance base.

Also disclosed is a fragranced product comprising the terpene blend prepared in accordance with the presently disclosed methods or a fragrance composition comprising the terpene blend and a fragrance product base.

Also disclosed is a method of preparing a fragranced product comprising mixing together the terpene blend prepared in accordance with the presently disclosed methods, or a fragrance composition comprising the terpene blend, with a fragrance product base.

Use of a terpene blend as a fragrance in a fragranced product is also provided, the terpene blend prepared by treating a feed containing nootkatol and at least one compound that catalyzes the conversion of nootkatol to nootkatene to mitigate or prevent conversion of nootkatol to nootkatene, and carrying out fractional distillation on the treated feed.

According to certain illustrative embodiments, provided is use of a terpene blend as a fragrance in a fragranced product, the terpene blend prepared by treating a feed containing nootkatol and at least one compound that catalyzes the conversion of nootkatol to nootkatene to mitigate or prevent conversion of nootkatol to nootkatene by separating at least a portion of the nootkatol from the catalyst compounds in the feed to create a second feed containing the nootkatol, and carrying out fractional distillation on the second feed.

According to certain illustrative embodiments, provided is use of a terpene blend as a flavour in a beverage or food product, the terpene blend prepared by treating a feed containing nootkatol and at least one compound that catalyzes the conversion of nootkatol to nootkatene to mitigate or prevent conversion of nootkatol to nootkatene by separating at least a portion of the nootkatol from the catalyst compound in the feed to create a second feed containing the nootkatol, and carrying out fractional distillation on the second feed.

According to certain illustrative embodiments, provided is use of a terpene blend as a fragrance in a fragrance product, the terpene blend prepared by providing a feed containing nootkatol and at least one compound that catalyzes the conversion of nootkatol to nootkatene, treating the feed to mitigate or prevent conversion by neutralizing at least a portion of the compounds present in the feed that catalyze the conversion of nootkatol to nootkatene, and carrying out fractional distillation on the treated feed.

According to certain illustrative embodiments, provided is use of a terpene blend as a flavour in a beverage or food product, the terpene blend prepared by providing a feed containing nootkatol and at least one compound that catalyzes the conversion of nootkatol to nootkatene, treating the feed to mitigate or prevent conversion by neutralizing at least a portion of the compounds present in the feed that catalyze the conversion of nootkatol to nootkatene, and carrying out fractional distillation on the treated feed.

DETAILED DESCRIPTION

Raw material terpene blends may contain nootkatols. As used in this specification, the term "nootkatol" includes α-nootkatol and β-nootkatol. According to certain embodiments, the raw material terpene blend includes at least one nootkatol. According to illustrative embodiments, the raw material terpene blend comprises α-nootkatol. According to other illustrative embodiments, the raw material terpene blend comprises β-nootkatol. According to further illustrative embodiments, the raw material terpene blend comprises both α-nootkatol and β-nootkatol.

Raw material terpene blends containing nootkatols may also contain acid compounds and other high boiling point impurities that catalyze the reaction of nootkatol to nootkatene at elevated temperatures utilized in typical fractional distillation processes conducted on the raw material terpene blend to prepare nootkatone blends for use as flavour or fragrance ingredients. Disclosed is a method for mitigating or preventing the conversion of nootkatol to nootkatene that typically occurs during a high temperature fractional distillation process carried out on a blend of terpenes containing nootkatol prior to conducting the fractional distillation process, such that the amount of nootkatene formed during the fractional distillation is reduced to commercially acceptable levels.

According to certain embodiments, the raw material terpene blend used in accordance with the presently disclosed methods contains at least α-nootkatol and at least one compound or molecule that catalyzes the chemical reaction from α-nootkatol to nootkatene. According to certain illustrative embodiments, the raw material terpene blend may comprise more than one nootkatol, such as a mixture of α-nootkatol and β-nootkatol, and the at least one compound or molecule that catalyzes the chemical reaction from α-nootkatol to nootkatene. According to further illustrative embodiments, the raw material blend may comprise α-nootkatol, β-nootkatol, β, γ-nootkatone, nootkene, nootkatone and valencene, and the at least one compound or molecule that catalyzes the chemical reaction from α-nootkatol to nootkatene.

According to certain embodiments, the raw material terpene blend may be prepared by microbial fermentation with suitable microbial organisms capable of carrying out the fermentation process to produce the terpene blend containing at least one nootkatol. The present disclosure is not limited to the use of terpene blends prepared by microbial fermentation, and raw material blends may contain nootkatols that have been extracted from grapefruit, Alaska yellow cedar trees, vetiver grasses, or compositions which contain sesquiterpene substrates, such as valencene, which can be oxidized to nootkatols by any means of oxidation, including, without limitation, chemical oxidation, enzymatic oxidation, or whole cell biotransformation. Methods of enzymatic oxidation of sesquiterpene substrates to oxygenated sesquiterpenes (for example, to nootkatol and/or nootkatone) are disclosed in WO 2016/029187 and WO 2016/029153, both of which are hereby incorporated by reference.

According to certain illustrative embodiments, the method for mitigating or preventing the conversion of nootkatols to nootkatene comprises separating a portion of the nootkatol present in a feed, such as a feed comprising a raw material terpene blend, from the one or more compounds that catalyze the chemical conversion of nootkatol to nootkatene that are also present in the material feed.

According to certain illustrative embodiments, the method for mitigating or preventing the conversion of nootkatols to nootkatene comprises neutralizing acid compounds present in a terpene blend or feed containing nootkatol that catalyze the chemical conversion of nootkatol to nootkatene.

According to certain illustrative embodiments, the method for mitigating or preventing the conversion of nootkatols to nootkatene comprises neutralizing acid compounds present in a terpene blend containing nootkatol that catalyze the chemical conversion of nootkatol to nootkatene, and subsequently separating the a portion of the nootkatol from remaining compounds that catalyze the chemical conversion of nootkatol to nootkatene.

According to the present method for mitigating or preventing the conversion of nootkatol to nootkatene, the nootkatol is either separated from the one or more compounds that catalyze the reaction from nootkatol to nootkatene in a shorter period of time and at lower temperatures than can be obtained with fractional distillation of the raw material terpene blend containing nootkatol, or the one or more compounds that catalyze the reaction from nootkatol to nootkatene are neutralized.

Separating the desirable terpenes, including α-nootkatol, from the compounds that catalyze the conversion of nootkatol to nootkatene, or neutralizing the catalyst compounds present within the raw material terpene blend, enables the terpene blend to be fractionally distilled at elevated temperatures and for an extended period of time without substantial losses to the total amount of nootkatol recovered from the fractional distillation process. According to certain illustrative embodiments, conducting the treating step of separating the desired terpenes from the catalyst compounds present within the raw material terpene blend, or neutralizing the catalyst compounds present within the raw material terpene blend, reduces the loss to the total amount of nootkatol recovered following fractional distillation to 10 weight percent or less as compared to the expected recovery of nootkatol following a fractional process without first conducting the disclosed treating step(s).

According to certain illustrative embodiments, the method of mitigating or preventing the conversion of nootkatol to nootkatene comprises separating at least a portion of nootkatol and other desired terpenes present in a terpene feed containing a blend of terpenes from one or more compounds that catalyze the conversion of nootkatol to nootkatene present in the terpene feed containing a blend of terpenes.

According to certain illustrative embodiments, the method of mitigating or preventing the conversion of nootkatol to nootkatene comprises providing a feed containing nootkatol, other desired terpene species, and at least one compound that catalyzes the conversion of nootkatol to nootkatene. At least a portion of the nootkatol present in the terpene feed is separated from the at least one compound that catalyzes the conversion of nootkatol to nootkatene and further processed.

According to certain illustrative embodiments, the method of mitigating or preventing the conversion of nootkatol to nootkatene comprises providing a feed containing a blend of terpenes, including nootkatol, other desired terpenes, and at least one compound that catalyzes the conversion of nootkatol to nootkatene. At least a portion of the nootkatol and at least a portion of the other desired terpenes present in the terpene feed are separated from the at least one compound that catalyzes the conversion of nootkatol to nootkatene.

According to certain illustrative embodiments, the one or more compounds present in the feed materials that catalyzes the conversion of nootkatol to nootkatene comprises at least one acid. The acid may comprise any acid-containing molecule that catalyzes the conversion of nootkatol to nootkatene. The acids include inorganic (mineral) acids and organic acids. According to certain embodiments, the acid that catalyzes the conversion of nootkatol to nootkatene comprises a fatty acid. For example, and without limitation the fatty acid may comprise a carboxylic acid and a hydrocarbon tail having from 2 to 28 carbon atoms. The hydrocarbon tail may be straight or branched and may contain ring structures. This includes short chain fatty acids, medium chain fatty acids and long chain fatty acids. The fatty acids may be selected from saturated or unsaturated fatty acids. The hydrocarbon tails of the unsaturated fatty acids may contain one or more double bonds. The hydrogen atoms adjacent to the double bonds of the hydrocarbon tails of the unsaturated fatty acids may assume either the cis or trans configurations. According to certain embodiments, and without limitation, illustrative examples of the at least one fatty acid are selected from pelargonic acid (C9:0), capric acid (C10:0), undecanoic acid (C11:0), lauric acid (C12:0), tridecanoic acid (C13:0), myristic acid (C14:0), pentadecanoic acid (C15:0), palmitic acid (C16:0), linoleic acid (C18:2), oleic acid (C18:1), elaidic acid (C18:1), stearic acid (C18:0) and combinations thereof.

According to certain embodiments, the step of separating the acid from the terpene feed containing the nootkatol and the acid that catalyzes the conversion of nootkatol to nootkatene comprises a distillation process. According to disclosed method, the distillation comprises a single stage distillation. According to certain embodiments, the single stage distillation process is carried out at a pot temperature of 25 to 260° C., a vapor temperature of 25 to 140° C., a pressure of 0 to 50 mmHg for 60 to 180 minutes. According to other embodiments, the single stage distillation process is carried out at a pot temperature of 140 to 240° C., a vapor temperature of 40 to 130° C., a pressure of 0 to 20 mmHg for 80 to 130 minutes. According to other embodiments, the single stage distillation process is carried out at a pot temperature of 160 to 200° C., a vapor temperature of 75 to 120° C., a pressure of 0 to 1 mmHg for 90 to 110 minutes.

According to certain illustrative embodiments, the conversion of nootkatol to nootkatene is mitigated by treating the feed containing the nootkatol and compounds that catalyze the conversion of nootkatol to nootkatene by adding a base to the feed. The base has the chemical property of neutralizing an acid or raising the pH of a liquid. Adding the base to the feed neutralizes at least a portion of the compounds present in the feed that catalyze the conversion of nootkatol to nootkatene, thereby mitigating or preventing the conversion to nootkatene.

The base that is added to the feed containing the nootkatol and one or more acid compounds that catalyze the conversion of nootkatol to nootkatene may be selected from any base that is capable of at least partially or fully neutralizing the one or more acid compounds. According to certain illustrative embodiments, the base that is added to the feed containing the nootkatol and one or more acid compounds that catalyze the conversion of nootkatol to nootkatene to at least partially neutralize the acid comprises at least one nitrogen-containing compound. According to certain illustrative embodiments, the nitrogen-containing compound that is added to the feed containing the nootkatol and one or more acid compounds that catalyze the conversion of nootkatol to nootkatene to at least partially neutralize the acid comprises at least one amine. According to certain illustrative embodiments, the amine compound that is added to the feed containing the nootkatol and one or more acid compounds that catalyze the conversion of nootkatol to nootkatene to at least partially neutralize the acid comprises at least one alkylamine. According to certain illustrative embodiments, the amine compound that is added to the feed containing the nootkatol and one or more acid compounds that catalyze the conversion of nootkatol to nootkatene to at least partially neutralize the acid comprises at least one secondary or tertiary amine. According to certain illustrative embodiments, the amine compound that is added to the feed containing the nootkatol and one or more acid compounds that catalyze the conversion of nootkatol to nootkatene to at least partially neutralize the acid comprises at least one trialkylamine. Without limitation, and only by way of illustration, the tertiary amine may be selected from one or more of trioctylamine, tridodecylamine and combinations thereof. According to other embodiments, the base that is added to the feed containing the nootkatol and one or more acid compounds that catalyze the conversion of nootkatol to nootkatene may be selected from hydroxide bases. Without limitation, and only by way of illustration, hydroxide bases include ammonium hydroxide, calcium hydroxide, lithium, magnesium hydroxide, potassium, sodium hydroxide and mixtures thereof.

According to other illustrative embodiments, the nitrogen-containing compound that is added to the feed containing the nootkatol and one or more acid compounds that catalyze the conversion of nootkatol to nootkatene to at least partially neutralize the acid comprises ammonia. According to certain embodiments, the ammonia is introduced into the feed as a gas by flowing the gaseous ammonia into the feed containing the nootkatol and one or more acid compounds that catalyze the conversion of nootkatol to nootkatene to at least partially neutralize the acid. According to certain embodiments, the step of flowing the ammonia gas into the feed containing the nootkatol and one or more acid compounds comprises sparging the ammonia gas into the feed.

According to certain embodiments, the method of mitigating or preventing the conversion of nootkatol to nootkatene comprises providing a feed containing nootkatol and at least one compound that catalyzes the conversion of nootkatol to nootkatene. At least a portion of the nootkatol, and one or more desired terpenes present in the feed, are separated from the at least one compound by distillation and the nootkatol is collected as the distillate. According to certain embodiments, at least a portion of the nootkatol, and one or more desired terpenes present in the feed, are separated from the at least one compound by a single stage distillation and the nootkatol is collected as the distillate.

According to certain embodiments, the method of preparing a nootkatone composition comprises providing a feed containing nootkatol and at least one compound that catalyzes the conversion of nootkatol to nootkatene. The feed is treated to mitigate or prevent conversion of nootkatol to nootkatene by separating the nootkatol from the feed by distillation to create a second feed containing the nootkatol and other desired terpenes, and collecting the nootkatol as the distillate. Fractional distillation is subsequently carried out on the treated feed containing the collected nootkatol distillate.

According to certain embodiments, the method of preparing a nootkatone composition comprises providing a feed containing nootkatol and at least one compound that catalyzes the conversion of nootkatol to nootkatene. The feed is treated to mitigate or prevent conversion by neutralizing compounds present in the feed that catalyze the conversion of nootkatol to nootkatene by adding a base to the feed. Fractional distillation carried out on the treated feed to produce the nootkatone composition.

In accordance with certain embodiments, by pre-treating a feed containing nootkatol and compounds that catalyze the chemical conversion of nootkatol to nootkatene, by separating at least a portion of the nootkatol from compounds present in the feed that catalyze the reaction of nootkatol to nootkatene, or by neutralizing the compounds present in the feed that catalyze the reaction of nootkatol to nootkatene with a neutralizing compound or molecule (such as a base), or by first separating at least a portion of the nootkatol from compounds present in the feed that catalyze the reaction of nootkatol to nootkatene followed by neutralizing the compounds present in the feed that catalyze the reaction of nootkatol to nootkatene with a neutralizing compound or molecule, the amount of nootkatol retained in terpene blend following fractional distillation is at least 50 weight percent, or at least 45 weight percent, or at least 40 weight percent, or at least 35 weight percent, or at least 30 weight percent, or at least 25 weight percent, or at least 20 weight percent, or at least 15 weight percent, or at least 10 weight percent.

In accordance with certain embodiments, by pre-treating a feed containing nootkatol and compounds that catalyze the chemical conversion of nootkatol to nootkatene, by separating at least a portion of the nootkatol from compounds present in the feed that catalyze the reaction of nootkatol to nootkatene, or by neutralizing the compounds present in the feed that catalyze the reaction of nootkatol to nootkatene with a neutralizing compound or molecule (such as a base), or by first separating at least a portion of the nootkatol from compounds present in the feed that catalyze the reaction of nootkatol to nootkatene followed by neutralizing the compounds present in the feed that catalyze the reaction of nootkatol to nootkatene with a neutralizing compound or molecule, the terpene blend following a fractional distillation step contains 1 weight percent or less nootkatene. According to other illustrative embodiments, the terpene blend prepared in accordance with the disclosed methods contains 0.9 weight percent or less, 0.8 weight percent or less, 0.7 weight percent or less, 0.6 weight percent or less, 0.5 weight percent or less, 0.4 weight percent or less, 0.3 weight percent or less, 0.2 weight percent or less, or 0.1 weight percent or less of nootkatene.

Also disclosed is a distillate fraction useful for preparing a terpene blend, the distillate fraction comprising at least 50 weight percent $\alpha$-nootkatol and 1 weight percent or less nootkatene, or at least 45 weight percent $\alpha$-nootkatol and 1 weight percent or less nootkatene, or at least 40 weight percent $\alpha$-nootkatol and 1 weight percent or less nootkatene, or at least 35 weight percent $\alpha$-nootkatol and 1 weight percent or less nootkatene, or at least 30 weight percent $\alpha$-nootkatol and 1 weight percent or less nootkatene, or at least 25 weight percent $\alpha$-nootkatol and 1 weight percent or less nootkatene, or at least 20 weight percent $\alpha$-nootkatol and 1 weight percent or less nootkatene, or at least 15 weight percent $\alpha$-nootkatol and 1 weight percent or less nootkatene, or at least 10 weight percent $\alpha$-nootkatol and 1 weight percent or less nootkatene.

According to certain embodiments, the distillate fraction useful for preparing a terpene blend comprises at least 50 weight percent $\alpha$-nootkatol and 1 weight percent or less nootkatene, or at least 45 weight percent $\alpha$-nootkatol and 0.5 weight percent or less nootkatene, or at least 40 weight percent $\alpha$-nootkatol and 0.5 weight percent or less nootkatene, or at least 35 weight percent $\alpha$-nootkatol and 0.5 weight percent or less nootkatene, or at least 30 weight percent $\alpha$-nootkatol and 0.5 weight percent or less nootkatene, or at least 25 weight percent $\alpha$-nootkatol and 0.5 weight percent or less nootkatene, or at least 20 weight percent $\alpha$-nootkatol and 0.5 weight percent or less nootkatene, or at least 15 weight percent $\alpha$-nootkatol and 0.5 weight percent or less nootkatene, or at least 10 weight percent $\alpha$-nootkatol and 0.5 weight percent or less nootkatene.

According to other illustrative embodiments, the distillate fraction useful for preparing a terpene blend comprises at least 50 weight percent $\alpha$-nootkatol and 1 weight percent or less nootkatene, or at least 45 weight percent $\alpha$-nootkatol and 0.25 weight percent or less nootkatene, or at least 40 weight percent $\alpha$-nootkatol and 0.25 weight percent or less nootkatene, or at least 35 weight percent $\alpha$-nootkatol and 0.25 weight percent or less nootkatene, or at least 30 weight percent $\alpha$-nootkatol and 0.25 weight percent or less nootkatene, or at least 25 weight percent $\alpha$-nootkatol and 0.25 weight percent or less nootkatene, or at least 20 weight percent $\alpha$-nootkatol and 0.25 weight percent or less nootkatene, or at least 15 weight percent $\alpha$-nootkatol and 0.25 weight percent or less nootkatene, or at least 10 weight percent $\alpha$-nootkatol and 0.25 weight percent or less nootkatene.

According to other illustrative embodiments, the distillate fraction useful for preparing a terpene blend comprises at least 50 weight percent $\alpha$-nootkatol and 1 weight percent or less nootkatene, or at least 45 weight percent $\alpha$-nootkatol and 0.1 weight percent or less nootkatene, or at least 40 weight percent $\alpha$-nootkatol and 0.1 weight percent or less nootkatene, or at least 35 weight percent $\alpha$-nootkatol and 0.1 weight percent or less nootkatene, or at least 30 weight percent $\alpha$-nootkatol and 0.1 weight percent or less nootkatene, or at least 25 weight percent $\alpha$-nootkatol and 0.1 weight percent or less nootkatene, or at least 20 weight percent $\alpha$-nootkatol and 0.1 weight percent or less nootkatene, or at least 15 weight percent $\alpha$-nootkatol and 0.1 weight percent or less nootkatene, or at least 10 weight percent $\alpha$-nootkatol and 0.1 weight percent or less nootkatene.

Also disclosed is a terpene blend prepared in accordance with the disclosed methods. The terpene blend may comprise a fractional distillate prepared in accordance with the presently disclosed methods, or may comprise blend of distillate fractions prepared in accordance with the presently disclosed methods, to achieve the desired concentration of one or more terpenes.

According to certain illustrative embodiments, the terpene blend may comprise from about 40 to about 60 weight percent nootkatone, or from about 40 to about 55 weight percent nootkatone, or from about 40 to about to about 50 weight percent nootkatone, or from about 45 to about 55 weight percent nootkatone, or from about 48 to about 52 weight percent nootkatone, or from about 49 to about 51 weight percent nootkatone, based on the total weight of the terpene blend.

According to certain illustrative embodiments, the terpene blend may comprise from about 5 to about 25 weight percent α-nootkatol, or from about 5 to about 20 weight percent α-nootkatol, or from about 5 to about 15 weight percent α-nootkatol, or from about 5 to about 10 weight percent α-nootkatol, or from about 10 to about 25 weight percent α-nootkatol, from about 10 to about 20 weight percent α-nootkatol, or from about 10 to about 15 weight percent α-nootkatol, or from about 12 to about 20 weight percent α-nootkatol, or from about 13.5 to about 17.5 weight percent α-nootkatol, or from about 15 to about 25 weight percent α-nootkatol, or from about 15 to about 20 weight percent α-nootkatol, based on the total weight of the terpene blend.

According to certain illustrative embodiments, the terpene blend may comprise from about 0.001 to about 5 weight percent β-nootkatol, or 0.01 to about 5 weight percent β-nootkatol, or 0.05 to about 5 weight percent β-nootkatol, or 0.1 to about 5 weight percent β-nootkatol, or 0.25 to about 5 weight percent β-nootkatol, or 0.5 to about 5 weight percent β-nootkatol, or 0.75 to about 5 weight percent β-nootkatol, or 0.3 to about 0.6 weight percent β-nootkatol, or 0.35 to about 0.45 weight percent β-nootkatol, or 1 to about 5 weight percent β-nootkatol, or 1.5 to about 5 weight percent β-nootkatol, or 2 to about 5 weight percent β-nootkatol, or 2.5 to about 5 weight percent β-nootkatol, or 3 to about 5 weight percent β-nootkatol, or 3.5 to about 5 weight percent β-nootkatol, or 4 to about 5 weight percent β-nootkatol, or 4.5 to about 5 weight percent β-nootkatol, based on the total weight of the terpene blend.

According to certain illustrative embodiments, the terpene blend may comprise from about 0.1 to about 5 weight percent β,γ-nootkatone, or about 0.25 to about 5 weight percent β,γ-nootkatone, or about 0.5 to about 5 weight percent β,γ-nootkatone, or about 0.75 to about 5 weight percent β,γ-nootkatone, or about 1 to about 5 weight percent β,γ-nootkatone, or about 1.5 to about 5 weight percent β,γ-nootkatone, or about 2 to about 5 weight percent β,γ-nootkatone, or about 2.5 to about 5 weight percent β,γ-nootkatone, or about 3 to about 5 weight percent β,γ-nootkatone, or about 3.5 to about 5 weight percent β,γ-nootkatone, or about 4 to about 5 weight percent β,γ-nootkatone, or about 4.5 to about 5 weight percent β,γ-nootkatone, or about 2 to about 3 weight percent β,γ-nootkatone, or about 2.5 to about 3 weight percent β,γ-nootkatone, based on the total weight of the terpene blend. According to certain illustrative embodiments, the terpene blend may comprise from about 5 weight percent or less β,γ-nootkatone, or from about 4 weight percent or less β,γ-nootkatone, or from about 3 weight percent or less β,γ-nootkatone, or from about 2 weight percent or less β,γ-nootkatone, or from about 1 weight percent or less β,γ-nootkatone, based on the total weight of the terpene blend.

According to certain illustrative embodiments, the terpene blend may comprise from about 0.01 to about 1 weight percent nootkatene, or 0.02 to about 1 weight percent nootkatene, or 0.03 to about 1 weight percent nootkatene, or 0.04 to about 1 weight percent nootkatene, or 0.05 to about 1 weight percent nootkatene, or 0.06 to about 1 weight percent nootkatene, or 0.07 to about 1 weight percent nootkatene, or 0.08 to about 1 weight percent nootkatene, or 0.09 to about 1 weight percent nootkatene, or 0.1 to about 1 weight percent nootkatene, or 0.15 to about 1 weight percent nootkatene, or 0.2 to about 1 weight percent nootkatene, or 0.25 to about 1 weight percent nootkatene, or 0.3 to about 1.25 weight percent nootkatene, or 0.3 to about 1 weight percent nootkatene, or 0.35 to about 1 weight percent nootkatene, or 0.4 to about 1 weight percent nootkatene, or 0.45 to about 1 weight percent nootkatene, or 0.5 to about 1 weight percent nootkatene, or 0.55 to about 1 weight percent nootkatene, or 0.6 to about 1 weight percent nootkatene, or 0.65 to about 1 weight percent nootkatene, or 0.7 to about 1 weight percent nootkatene, or 0.75 to about 1 weight percent nootkatene, or 0.8 to about 1 weight percent nootkatene, or 0.85 to about 1 weight percent nootkatene, or 0.9 to about 1 weight percent nootkatene, or 0.95 to about 1 weight percent nootkatene, based on the total weight of the terpene blend.

According to certain illustrative embodiments, the terpene blend may comprise from about 0.001 to about 15 weight percent valencene, or from about 0.01 to about 15 weight percent valencene, or from about 0.025 to about 15 weight percent valencene, or from about 0.05 to about 15 weight percent valencene, or from about 0.075 to about 15 weight percent valencene, or from about 0.1 to about 15 weight percent valencene, or from about 0.25 to about 15 weight percent valencene, or from about 0.5 to about 15 weight percent valencene, or from about 0.75 to about 15 weight percent valencene, or from about 0.03 to about 1.5 weight percent valencene, or from about 0.03 to about 0.55 weight percent valencene, or from about 0.4 to about 1.5 weight percent valencene, or from about 1 to about 15 weight percent valencene, or from about 5 to about 15 weight percent valencene, or from about 10 to about 15 weight percent valencene, or from about 5 to about 10 weight percent valencene, based on the total weight of the terpene blend.

According to certain illustrative embodiments, the terpene blend may comprise from about 5 to about 25 weight percent α-nootkatol, from about 0.001 to about 5 weight percent β-nootkatol, from about 0.1 to about 5 weight percent β,γ-nootkatone, from about 40 to about 60 weight percent nootkatone, from about 0.01 to about 1 weight percent nootkatene and from about 0.001 to about 15 weight percent valencene, based on the total weight of the terpene blend.

According to certain illustrative embodiments, the terpene blend may comprise from about 12 to about 20 weight percent α-nootkatol, from about 0.3 to about 0.6 weight percent β-nootkatol, from about 2.5 to about 3 weight percent β,γ-nootkatone, from about 48 to about 52 weight percent nootkatone, from about 0.3 to about 1.2 weight percent nootkatene and from about 0.4 to about 1.5 weight percent valencene, based on the total weight of the terpene blend.

According to certain illustrative embodiments, the terpene blend may comprise from about 12 to about 20 weight percent α-nootkatol, from about 0.3 to about 0.6 weight percent β-nootkatol, from about 2.5 to about 3 weight percent β,γ-nootkatone, from about 48 to about 52 weight percent nootkatone, from about 0.3 to about 1.2 weight percent nootkatene and from about 0.4 to about 1.5 weight percent valencene, from about 0.2 to about 0.5 weight percent 1,10 dihydronootkatone, and from about 25 to about 30 weight percent other sesquiterpenes, based on the total weight of the terpene blend.

According to certain illustrative embodiments, the terpene blend may comprise from about 13.5 to about 17 weight percent α-nootkatol, from about 0.35 to about 0.45 weight percent β-nootkatol, from about 0.55 to about 1.4 weight percent β,γ-nootkatone, from about 49 to about 51 weight percent nootkatone, from about 0.3 to about 1 weight percent nootkatene and from about 0.03 to about 0.55 weight percent valencene, based on the total weight of the terpene blend.

According to certain illustrative embodiments, the terpene blend may comprise from about 13.5 to about 17 weight percent α-nootkatol, from about 0.35 to about 0.45 weight percent β-nootkatol, from about 0.55 to about 1.4 weight percent β,γ-nootkatone, from about 49 to about 51 weight percent nootkatone, from about 0.3 to about 1 weight percent nootkatene and from about to about 0.55 weight percent valencene, from about 0.2 to about 0.35 weight percent 1,10 dihydronootkatone, and from about 25 to about 30 weight percent other sesquiterpenes, based on the total weight of the terpene blend.

A fragrance composition containing the terpene blend prepared in accordance with the present disclosure may further include one or more additional fragrance compounds.

According to certain illustrative embodiments, without limitation, the additional fragrance compounds may include one or more aldehydic compound(s), one or more balsamic compound(s), one or more different citrus compound(s), one or more floral compound(s), one or more fruity compound(s), one or more gourmand compound(s), one or more green compound(s), one or more marine compound(s), one or more mossy compound(s), one or more musk compound(s), one or more piney compound(s), one or more spicy compound(s), and/or one or more woody compound(s), or combinations thereof.

By way of illustration, and not in limitation, suitable aldehydic compounds include saturated alkyl aldehydes including, but not limited to, ALDEHYDE C 12 MNA (2-methylundecanal); ALDEHYDE C 8 OCTYLIC (octanal); ALDEHYDE C 9 (nonanal); ALDEHYDE C 6 HEXYLIC (hexanal); CALYPSONE (6-methoxy-2,6-dimethyloctanal); ALDEHYDE C 7 HEPTYLIC (heptanal); ALDEHYDE C 10 decanal; ALDEHYDE C 12 dodecanal; acetaldehyde; n-butyraldehyde; isobutraldehyde. In one embodiment, the saturated alkyl aldehydes are selected from the group consisting of ALDEHYDE C 12 MNA and CALYPSONE.

In another embodiment, suitable odor-reducing materials include unsaturated alkyl aldehydes including, but not limited to, DECEN-1-AL, CIS-4 ((Z)-dec-4-enal); DECENAL-4-TRANS ((E)-dec-4-enal); DECENAL-9 (9-decenal), MELONAL (2,6-dimethylhept-5-enal); CYCLAL C (2,4-dimethylcyclohex-3-enecarbaldehyde); NONADIENAL ((2E,6Z)-nona-2,6-dienal); PINOACETALDEHYDE β-(6,6-dimethylbicyclo[3.1.1]hept-2-en-2-yl)propanal); SHISOLIA (4-vinylcyclohex-1-enecarbaldehyde); MACEAL (bicyclo[2.2.2]oct-5-ene-2-carboxaldehyde); cinnamic aldehyde; citronellal; trans-2-hexenal; trans 2-decenal, cis-3-hexenal and cis-4-heptenal. In one embodiment, the unsaturated alkyl aldehydes are selected from the group consisting of MELONAL, CYCLAL C, SHISOLIA and MACEAL.

In another embodiment, suitable odor-reducing materials include aromatic aldehydes including, but not limited to, anisyl aldehyde; AUBEPINE PARA CRESOL (4-methoxybenzaldehyde), FLORHYDRAL (3-(3-isopropylphenyl)butanal); benzaldehyde; PHENYL PROPIONIC ALDEHYDE (3-phenylpropanal); and TOLYL ALDEHYDE PARA (4-methylbenzaldehyde).

By way of illustration, and not in limitation, suitable citrus compounds may include citral, citronellal, L-citronellol, decanal, limonene, myrcenol, sinensal, bergamot oil, grapefruit oil, lemon oil, lime oil, and/or orange oil.

By way of illustration, and not in limitation, suitable floral compound can be anisyl acetate, anisic aldehyde, benzyl acetate, bourgeonal, butyl acetate, cyclamen aldehyde, cyclohexyl lactone, delta-damascone, farnesal, L-farnesal, farnesol, florhydral, floralozone, geraniol, gernayl acetate, piperonal, hedione, heliobouquet, hexyl cinnamaldehyde, hexyl salicylate, indole, alpha-ionone, beta-ionone, isopropoxy ethyl salicylate, jasmodione, cis-jasmone, kovanol, laurinol, linalool, linalyl acetate, mayol, methyl dihydrojasomante, .gamma.-methyl ionone, methoxymelonal, nerol, nerolione, neryl acetate, 2-pentyl cyclopentanone, phenoxanol, phenoxy ethyl isobutyrate, phenylacetaldehyde, phenyl ethyl alcohol, rose oxide, suzaral, undecavertol, geranium oil, lavender oil, rose oil, and/or ylang oil. A fruity compound can be aldehyde C-C16, allyl caproate, allyl cyclohexyl proprionate, allyl heptanoate, amyl acetate, benzaldehyde, L-citronellyl acetate, L-citronellyl nitrile, cyclacet, damascenone, beta-decalactone, gamma-decalactone, diethyl malonate, dimethyl phenyl ethyl carbinol, dimethyl sulfide, gamma-dodecalactone, ethyl acetate, ethyl butyrate, ethyl caproate, ethyl decadienotate, ethyl-2-methylbutyrate, ethyl acetoacetate, ethyl propionate, florol, hexyl acetate, hexyl isobutyrate, isoamyl acetate, jasmolactone, manzanate, melonal, methyl heptyl ketone, gamma-nonalactone, gamma-octalactone, phenyl ethyl isobutyrate, raspberry ketone, ringonol, thesaron, tolyl aldehyde, gamma-undecalactone, vanoris, and/or verdox.

By way of illustration, and not in limitation, suitable gourmand compounds may include caprylic acid, coumarin, ethyl fraison, ethyl vanillin, ethyl maltol, filbertone, furaneol, guaiacol, maple furanone, 2-acetyl pyrazine, 2,5-dimethyl pyrazine, and/or vanillin.

By way of illustration, and not in limitation, suitable green compounds may include dynascone, galbanolene, trans-2-hexenal, cis-3-hexenol, hexen-1-ol, cis-3-hexenyl acetate, cis-3-hexenyl butyrate, cis-3-hexenyl salicyclate, liffarome, methyl octine carbonate, 2,6-nonadienal, oxane, stemone, styrallyl acetate, triplal, undecavertol, violet methyl carbonate, vionil, and/or violet leaf extract.

By way of illustration, and not in limitation, suitable musk compounds may include ambrettolide, ambretone, ambroxan, exaltolide, galaxolide, habanolide, helvetolide, (1R)-3-methyl-5-(2,2,3-trimethylcyclopentan-1-yl)-2-pentanone, muscenone, musk T, L-muscone, and/or tonalid.

By way of illustration, and not in limitation, suitable piney compounds may include alpha-pinene, beta-pinene and mixture thereof.

By way of illustration, and not in limitation, suitable spicy compounds may include .beta.-caryophellene, cinnamaldehyde, cuminaldehyde, eugenol, isoeugenol, perilla aldehyde, cardamom oil, clove oil, ginger extract and/or black pepper extract.

By way of illustration, and not in limitation, suitable woody compounds may include amber core, amber extreme, ambroxan, bacdanol, cedramber, cedanol, ebanol, hindinol, hinokitiol, javanol, norlimbanol dextro, osyrol, patchone, polyambrol, .alpha.-pinene, .beta.-pinene, sandalmysore core, sandalore, santalex T, orbitone, cedarwood oil, patchouli oil, sandalwood oil, and/or vetiver oil.

The terpene blend of the present disclosure may be included in a wide variety of food and beverage products.

The terpene blend of the present disclosure may be included in a wide variety of foods products that would benefit from a citrus aroma and/or flavour.

Muffins (e.g., English muffins), crackers (e.g., salted crackers, baked crackers, graham crackers, etc.), rolls (e.g., soft rolls, dinner rolls, crescent rolls), biscuits (e.g., buttermilk biscuits, cobbler biscuits), pie crusts, breads (e.g., focaccia, bruschetta, sourdough breads, soda breads, breadsticks, corn bread, etc.), bagels, brownies, cookies, turnovers, doughnuts, cakes, pastries, pies, scones, and the like.

Without limitation, and only by way of illustration, exemplary dairy products include ice cream, impulse ice cream, ice cream desserts, frozen yoghurt, milk, fresh/pasteurized milk, full fat fresh/pasteurized milk, semi skimmed fresh/pasteurized milk, long-life/UHT milk, full fat long life/UHT milk, semi skimmed long life/UHT milk, fat-free long life/UHT milk, goat milk, condensed/evaporated milk, plain condensed/evaporated milk, flavoured, functional and other condensed milk, flavoured milk drinks, dairy only flavoured milk drinks, soy milk, sour milk drinks, fermented dairy drinks, coffee creamers/whiteners, powder milk, flavoured powder milk drinks, cream, yoghurt, plain/natural yoghurt, flavoured yoghurt, fruited yoghurt, probiotic yoghurt, yoghurt drinks, and other dairy-based desserts.

Without limitation, and only by way of limitation, exemplary savoury food products include, salty snacks (potato chips, crisps, nuts, tortilla-tostada, pretzels, cheese snacks, corn snacks, potato-snacks, ready-to-eat popcorn, microwaveable popcorn, pork rinds, nuts, crackers, cracker snacks, breakfast cereals, meats, cured meats, luncheon/breakfast meats, tomato products, peanut butter, soups, canned vegetables, pasta sauces, and savoury biscuits, crackers and bread substitutes.

Without limitation, and only by way of illustration, sweet products include breakfast cereals, ready-to-eat ("rte") cereals, family breakfast cereals, flakes, muesli, other rte cereals, children's breakfast cereals, and hot cereals.

The terpene blend and/or flavour composition including the terpene blend of the present disclosure may be included in citrus beverages. Suitable citrus beverages include, without limitation, alcoholic citrus cocktails, citrus-flavoured drinks, citrus liqueurs, citrus-flavoured sodas, citrus-flavoured soft drinks, citrus-flavoured waters, citrus-flavoured still water, citrus-flavoured carbonated water, and the like. The terpene blend and/or flavour compositions including the terpene blend of the present disclosure may be included in tropical flavour compositions or foods and beverages containing tropical flavours (such as, for example, coconut, guava, kiwi, mango, papaya, passion fruit and pineapple flavour) containing citrus components.

The terpene blends and flavour compositions containing the terpene blends may be used in personal care products such as pharmaceuticals, cosmetics, and toiletries.

When used within cosmetics and toiletries, the formulations can be used in any of the "Reported Product Categories" listed by the Cosmetic, Toiletries and Fragrance Association's 'International Cosmetic Ingredient Dictionary and Handbook', and with any one or more of the ingredients cited as being used for the reported product categories. The Reported Product Categories include: aftershave lotions, baby lotions, oils, powders and creams, baby products miscellaneous, baby shampoos, basecoats and undercoats, bath capsules, bath oils, tablets and salts, bath preparations miscellaneous, bath soaps and detergents, beard softeners, blushers, body and hand preparations, bubble baths, cleaning products, colognes and toilet waters, cuticle softeners, dentifrices, deodorants, depilatories, douches, eye lotions, eye makeup preparations miscellaneous, eye makeup removers, eye shadows, eyebrow pencils, eyeliners, face and neck preparations, face powders, feminine hygiene deodorants, foot powders and sprays, foundations, fragrance preparations miscellaneous, hair bleaches, hair colour sprays, hair colouring preparations miscellaneous, hair conditioners, hair dyes and colours, hair lighteners with colour, hair preparations, hair rinses, hair shampoos, hair sprays, hair straighteners, hair tints, hair wave sets, indoor tanning preparations, leg and body paints, lipsticks, makeup bases, makeup fixatives, makeup preparations, manicuring preparations miscellaneous, mascara, men's talcum, moisturising preparations, mouthwashes and breath fresheners, nail creams and lotions, nail extenders, nail polish and enamel removers, nail polish and enamels, night skin care preparations, oral hygiene products miscellaneous, paste masks, perfumes, permanent waves, personal cleanliness products miscellaneous, powders, preshave lotions, rouges, sachets, shampoos, shaving cream, shaving preparations miscellaneous, shaving soap, skin care preparations miscellaneous, skin fresheners, suntan gels, creams and liquids, suntan preparations miscellaneous, sonics, dressings and other hair grooming aids.

The "oral care" or "oral hygiene" products may include any product that is applied to the oral cavity for the purposes of cleaning, freshening, healing, deodorizing the oral cavity or any part thereof. Without limitation, and only by way of illustration, such oral care and oral hygiene compositions include, toothpastes, tooth gels, tooth powders, tooth whitening products, mouth rinses, mouthwashes, gargle compositions, lozenges, dental floss, tooth picks, anti-plaque and anti-gingivitis compositions, throat lozenges, throat drops, compositions for treatment of nasal symptoms, cold symptoms, and for cold relief.

The nootkatone oil composition of the present disclosure may be included in a wide variety of other consumer products. Without limitation, and only by way of illustration, the consumer product may be selected from a fine fragrance, a home care product, and an air care product.

According to certain illustrative embodiments, and without limitation, the fine fragrance product may be selected from parfum, extrait de parfum, eau de parfum, millesime, parfum de toilette, eau de toilette, eau de cologne, body splash, after shave, body mists, and baby colognes.

According to certain illustrative embodiments, and without limitation, the home care product may be selected from fabric conditioner, fabric softener, laundry detergent, laundry additive, rinse additive, bleach, dryer sheets, perfume beads, car care products, dishwashing detergent, and hard surface cleaners.

According to certain illustrative embodiments, and without limitation, the air care product may be selected from a candle, aerosol, air freshener, liquid electric air freshener, fragrance diffuser, gel air freshener, plug-in air freshener, plug-in oil, and wax melt.

EXAMPLES

The following examples are set forth to describe illustrative embodiments of the disclosed methods in further detail and to illustrate the methods of mitigating or preventing the conversion of α-nootkatol to nootkatene in a terpene blend. The examples should not be construed as limiting the mitigating the chemical conversion of α-nootkatol to nootkatene in terpene blend feed, methods of making terpene blends, terpene blends, flavour compositions, fragrance compositions, beverage products, food products, fragrance products, methods of making beverage products, methods of making food products, and methods of making fragranced products

Comparative Example 1

A raw material blend of citrus terpenes containing about 1.61% total fatty acids was fractionally distilled under full vacuum. Table 1A below shows the initial amount of each of the components of the raw material terpene blend, and the amount of each component that was recovered from a high temperature fractional distillation process typically used to prepare nootkatone blends for use as flavour and fragrance ingredient. Table 1B below shows the temperature and composition of the distillate fractions as the fractional distillation progressed.

The results of the fractional distillation show that there was a significant reduction in the mass of nootkatols, and a corresponding increase in nootkatene mass during the batch fractional distillation process. There is also nootkatene present at >=1% in each distillate fraction except the first fraction, which is evidence of its continuous formation throughout the fractional distillation process.

Comparative Example 2/Examples 3-4

Samples of the same raw material blend of citrus terpenes containing about 1.61% total fatty acids used in Comparative Example 1 were evaluated to determine the effect of a simple one-stage distillation (Example 3) or treatment of the raw material terpene blend with a base material (Example 4) on the catalyzed reaction of α-nootkatol to nootkatene. Five weight percent of trioctylamine was added to the terpene blend of Example 4 as the basic material. Samples were heated for five hours at 1ATM with reflux and under a nitrogen pad with temperatures reaching up to 130° C. Tables 2A-2C below show the amounts (in grams) of nootkatols, nootkatene, nootkatones and other components present in the terpene blend charged into the reaction vessel (ie, flask) and recovered following the heat treatment.

TABLE 1A

|  | Valencene | Alpha-Nootkatol | Beta-Nootkatol | Beta-Gamma Nootkatone | Nootkatene | Nootkatone | Other |
|---|---|---|---|---|---|---|---|
| In RM sample #6 (g): | 87.2 | 88.7 | 2.3 | 4.6 | 1.5 | 323.2 | 244 |
| Recovered in cumulative dist. Fractions (g): | 73.1 | 37.7 | 1.8 | 22.8 | 39.2 | 277.6 | 224 |
| Fractionated yield from WFE distillate (%): | 84% | 43% | 76% | 500% | 2534% | 86% | 92% |
| Overall Yield from Oil sample (%): | 84% | 43% | 76% | 500% | 2534% | 86% | 92% |

TABLE 1B

| Fraction | Bottom Temp (° C.) | Valencene etc. | Alpha-Nootkatol | Beta-Nootkatol | Beta-Gammatone | Nootkatene | Nootkatone | Other |
|---|---|---|---|---|---|---|---|---|
| 1 | 173 | 57.10% | 0.00% | 0.00% | 0.00% | 0.03% | 0.03% | 43% |
| 2 | 177 | 65.70% | 0.00% | 0.00% | 0.00% | 4.40% | 0.00% | 30% |
| 3 | 184 | 61.50% | 0.00% | 0.00% | 0.00% | 9.69% | 0.00% | 29% |
| 4 | 159 | 40.40% | 0.07% | 0.00% | 0.00% | 19.00% | 0.00% | 41% |
| 5 | 196 | 2.00% | 15.70% | 0.14% | 1.39% | 10.46% | 4.52% | 66% |
| 6 | 199 | 0.10% | 21.40% | 0.37% | 3.15% | 13.10% | 14.90% | 47% |
| 7 | 201 | 0.03% | 13.70% | 0.70% | 3.98% | 3.72% | 44.60% | 33% |
| 8 | 203 | 0.04% | 8.90% | 0.62% | 5.88% | 4.27% | 50.10% | 30% |
| 9 | 203 | 0.04% | 2.85% | 0.46% | 6.46% | 2.87% | 59.10% | 28% |
| 10 | 204 | 0.02% | 0.81% | 0.24% | 4.44% | 1.26% | 69.90% | 23% |
| 11 | 208 | 0.02% | 0.48% | 0.16% | 3.86% | 1.07% | 71.80% | 23% |
| 12 | 211 | 0.02% | 0.43% | 0.11% | 4.00% | 1.37% | 71.10% | 23% |
| 13 | 222 | 0.03% | 0.59% | 0.15% | 4.51% | 2.99% | 70.00% | 22% |
| 14 | 244 | 0.09% | 0.50% | 0.26% | 4.28% | 6.81% | 64.50% | 24% |
| 15 | 261 | 0.30% | 0.00% | 0.18% | 4.70% | 8.23% | 55.50% | 31% |

TABLE 2A

Comparative/Control Example 2

| | Valencene | Alpha-Nootkatol | Beta-Nootkatol | Beta-Gamma-Nootkatol | Nootkatene | Nootkatone | Other |
|---|---|---|---|---|---|---|---|
| Sample charged to flask (g) | 5.8 | 5.9 | 0.2 | 0.3 | 0.1 | 21.5 | 16 |
| Recovered (g) | 6.4 | 0.0 | 0.0 | 0.8 | 5.2 | 20.9 | 16 |
| Five hour heat with reflux yield (%) | 110 | 0 | 0 | 276 | 5082 | 97 | 96 |

TABLE 2B

Example 3

| | Valencene | Alpha-Nootkatol | Beta-Nootkatol | Beta-Gamma-Nootkatol | Nootkatene | Nootkatone | Other |
|---|---|---|---|---|---|---|---|
| Sample charged to flask (g) | 5.6 | 4.9 | 0.1 | 0.1 | 0.3 | 22.0 | 17 |
| Recovered (g) | 5.9 | 0.5 | 0.2 | 0.5 | 3.8 | 22.0 | 17 |
| Five hour heat with reflux yield (%) | 104 | 10 | 129 | 751 | 1454 | 100 | 99 |

TABLE 2C

Example 4

| | Valencene | Alpha-Nootkatol | Beta-Nootkatol | Beta-Gamma-Nootkatol | Nootkatene | Nootkatone | Other |
|---|---|---|---|---|---|---|---|
| Sample charged to flask (g) | 5.8 | 5.9 | 0.2 | 0.3 | 0.1 | 21.5 | 16 |
| Recovered (g) | 5.8 | 1.7 | 0.1 | 0.3 | 2.5 | 22.0 | 20 |
| Five hour heat with reflux yield (%) | 100 | 28 | 88 | 113 | 2453 | 102 | 123 |

The simple distillate (Example 3) and amine spike (Example 4) both resulted in less nootkatene formation and retention of nootkatols. The conversion reaction from nootkatol to nooktene did occur in Examples 3 and 4, but at a far lesser extent as compared to Comparative/Control Example 2. The simple distillation (Example 3) conducted did carryover a limited amount of undesirable high boiling material, including some level of acidity. Based on these results, without being bound by any particular theory, if this process was terminated at a lower pot temperature the carryover of acidity and other high boiling point material could be further reduced or even eliminated, which would improve nootkatol stability over the results shown above for Example 3. Alternatively, a larger addition of tertiary amine to the raw material terpene blend may result in greater nootkatol stability and less formation of nootkatene as compared to Example 4.

Examples 5-6

A raw material blend of citrus terpenes containing about 1.61% total fatty acids was processed in accordance with embodiments of the disclosure. Fractional distillation was carried out on two samples of the same raw material blend of citrus terpenes following a either a simple one-stage distillation (Example 5) or the addition of 5 weight percent of a base, trioctylamine, (Example 6) to the terpene blend. Tables 3A and 3C below shows the temperature and composition of the distillate fractions as the fractional distillation progressed. Tables 3B-3D below show the amounts (in grams) of nookatols, nootkatene, nootkatones and other components present in the terpene blend charged into the reaction vessel (ie, flask) and recovered following the heat treatment.

TABLE 3A (Example 5)

| Fraction | Bottom Temp (° C.) | Valencene etc. (%) | Alpha-Nootkatol | Beta-Nootkatol | Beta-Gammatone (%) | Nootkatene | Nootkatone | Other (%) |
|---|---|---|---|---|---|---|---|---|
| 1 | 173 | 65.6% | 0.1% | 0.0% | 0.0% | 1.1% | 0.0% | 33.2% |
| 2 | 175 | 69.8% | 0.0% | 0.0% | 0.0% | 1.5% | 0.0% | 28.6% |
| 3 | 175 | 65.3% | 0.1% | 0.0% | 0.0% | 2.4% | 0.1% | 32.2% |

TABLE 3A-continued (Example 5)

| Fraction | Bottom Temp (° C.) | Valencene etc. (%) | Alpha-Nootkatol | Beta-Nootkatol | Beta-Gammatone (%) | Nootkatene | Nootkatone | Other (%) |
|---|---|---|---|---|---|---|---|---|
| 4 | 183 | 43.4% | 1.4% | 0.0% | 0.0% | 3.4% | 0.3% | 51.6% |
| 5 | 186 | 8.0% | 4.2% | 0.0% | 0.1% | 2.3% | 0.2% | 85.2% |
| 6 | 187 | 0.5% | 14.5% | 0.1% | 0.4% | 1.6% | 0.8% | 82.1% |
| 7 | 189 | 0.1% | 38.9% | 0.4% | 1.5% | 2.2% | 3.5% | 53.5% |
| 8 | 192 | 0.0% | 44.6% | 0.7% | 2.4% | 1.3% | 11.9% | 39.2% |
| 9 | 194 | 0.0% | 38.2% | 0.7% | 3.4% | 1.0% | 21.9% | 34.7% |
| 10 | 194 | 0.5% | 24.4% | 0.7% | 2.8% | 0.6% | 41.4% | 30.1% |
| 11 | 196 | 0.0% | 13.2% | 0.6% | 3.3% | 0.4% | 53.1% | 29.3% |
| 12 | 198 | 0.0% | 2.3% | 0.2% | 2.7% | 0.1% | 70.6% | 24.0% |
| 13 | 203 | 0.0% | 0.3% | 0.0% | 2.8% | 0.1% | 74.3% | 22.7% |
| 14 | 228 | 0.0% | 0.4% | 0.0% | 2.7% | 0.5% | 76.1% | 20.3% |
| 15 | 250 | 0.1% | 2.0% | 0.2% | 2.8% | 2.7% | 70.2% | 22.0% |

TABLE 3B

| | Valencene | Alpha-Nootkatel | Beta-Nootkatol | Beta-Gamma Nootkatone | Nootkatene | Nootkatone | Other |
|---|---|---|---|---|---|---|---|
| In sample (g): | 87.0 | 88.5 | 2.3 | 4.5 | 1.5 | 322.7 | 244 |
| Recovered in Simple Distillate (g): | 65.3 | 73.9 | 1.6 | 0.0 | 2.2 | 300.5 | 241 |
| Recovered in cumulative dist. Fractions (g): | 69.9 | 68.9 | 1.6 | 13.1 | 6.0 | 257.2 | 209 |
| Simple Distillation Yield (%): | 75% | 83% | 71% | 0% | 140% | 93% | 99% |
| Fractionated yield from distillate (%): | 107% | 93% | 98% | 0% | 276% | 86% | 87% |
| Overall Yield from Oil sample (%): | 80% | 78% | 70% | 288% | 388% | 80% | 86% |

TABLE 3C (Example 6)

| Fraction | Bottom Temp (° C.) | Valencene etc. (%) | Alpha-Nootkatol (%) | Beta-Nootkatol (%) | Beta-Gammatone (%) | Nootkatene | Nootkatone | Other (%) |
|---|---|---|---|---|---|---|---|---|
| 1 | 174 | 69.90% | 0.03% | 0.00% | 0.00% | 0.41% | 0.05% | 31% |
| 2 | 180 | 68.90% | 0.03% | 0.00% | 0.00% | 0.41% | 0.05% | 31% |
| 3 | 183 | 68.90% | 0.03% | 0.00% | 0.00% | 0.41% | 0.05% | 31% |
| 4 | 186 | 35.90% | 0.93% | 0.00% | 5.27% | 1.71% | 0.22% | 56% |
| 5 | 187 | 0.79% | 15.50% | 0.11% | 0.79% | 0.95% | 1.42% | 80% |
| 6 | 190 | 0.17% | 24.60% | 0.19% | 1.46% | 1.81% | 1.65% | 70% |
| 7 | 191 | 0.05% | 43.00% | 0.45% | 2.98% | 1.16% | 5.81% | 47% |
| 8 | 192 | 0.03% | 44.60% | 0.60% | 4.79% | 0.99% | 12.20% | 37% |
| 9 | 197 | 0.02% | 25.60% | 0.61% | 4.30% | 0.51% | 36.90% | 32% |
| 10 | 200 | 0.01% | 7.30% | 0.33% | 3.99% | 0.19% | 61.80% | 26% |
| 11 | 203 | 0.01% | 1.53% | 0.16% | 3.94% | 0.11% | 69.20% | 25% |
| 12 | 210 | 0.01% | 0.15% | 0.05% | 4.04% | 0.14% | 71.40% | 24% |
| 13 | 224 | 0.03% | 0.12% | 0.00% | 4.49% | 0.42% | 71.90% | 23% |
| 14 | 248 | 0.12% | 0.86% | 0.15% | 2.93% | 1.46% | 63.80% | 31% |

TABLE 3D

|  | Valencene | Alpha-Nootkatol | Beta-Nootkatol | Beta-Gamma Nootkatone | Nootkatene | Nootkatone | Other |
|---|---|---|---|---|---|---|---|
| In sample (g): | 81.4 | 82.8 | 2.1 | 4.3 | 1.4 | 301.7 | 228 |
| Charged to Pot for distillation (g): | 81.4 | 82.8 | 2.1 | 4.3 | 1.4 | 301.7 | 228 |
| Recovered in cumulative dist. Fractions (g): | 67.7 | 71.0 | 1.5 | 20.3 | 3.1 | 239.3 | 205 |
| Fractionated yield from distillate (%): | 83% | 86% | 70% | 478% | 215% | 79% | 90% |
| Overall Yield from Oil sample (%): | 83% | 86% | 70% | 478% | 215% | 79% | 90% |

Yields of α-nootkatol for both the amine-spiked (Example 6) and simple distillate fractionations (Example 5) were improved from 43% (Table, 1A comparative/control) to 86% and 93%, respectively. Both the simple distillation and amine pre-treatments were effective in retaining α-nootkatol and reducing the formation of nootkatene during fractional distillation. It is believed that the tertiary amine buffered the pH of the sample to prevent acidity from catalyzing the reaction, and the simple distillation separated the desirable terpenes from the higher boiling fatty acids. The nootkatene concentration in distillate fractions in Tables 3A and 3C are much lower overall compared to those fractions from the distillation of the untreated terpene blend samples.

It should be understood that when a range of values is described in the present disclosure, it is intended that any and every value within the range, including the end points, is to be considered as having been disclosed. For example, "a range of from 50 to 100" of a component is to be read as indicating each and every possible number along the continuum between 50 and 100. It is to be understood that the inventors appreciate and understand that any and all values within the range are to be considered to have been specified, and that the inventors have possession of the entire range and all the values within the range.

In the present disclosure, the term "about" used in connection with a value is inclusive of the stated value and has the meaning dictated by the context. For example, it includes at least the degree of error associated with the measurement of the particular value. One of ordinary skill in the art would understand the term "about" is used herein to mean that an amount of "about" of a recited value produces the desired degree of effectiveness in the compositions and/or methods of the present disclosure. One of ordinary skill in the art would further understand that the metes and bounds of "about" with respect to the value of a percentage, amount or quantity of any component in an embodiment can be determined by varying the value, determining the effectiveness of the compositions for each value, and determining the range of values that produce compositions with the desired degree of effectiveness in accordance with the present disclosure. The term "about" is further used to reflect the possibility that a composition may contain trace components of other materials that do not alter the effectiveness or safety of the composition.

Any compositional weight percentages disclosed herein are based on the total weight of the terpene blends, flavour compositions, fragrance compositions, food products, beverage products, or fragranced products, as the situation dictates. It will be understood to one of ordinary skill in the art that the total weight percent of the particular blend, composition or product cannot exceed 100%. For example, a person of ordinary skill in the art would easily recognize and understand that a beverage product comprising 50 to 95 weight percent of a beverage base and 5 to 50 weight percent of a terpene-based flavour composition will not exceed 100%. A person of ordinary skill in the art would understand that the amount of the components may be adjusted to include the desired amount of component without exceeding 100% by weight of the blends, compositions, or products.

The foregoing text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein.

While the methods of mitigating the chemical conversion of α-nootkatol to nootkatene in terpene blend feed, methods of making terpene blends, terpene blends, flavour compositions, fragrance compositions, beverage products, food products, fragrance products, methods of making beverage products, methods of making food products, and methods of making fragranced products have been described in connection with various illustrative embodiments, it is to be understood that other similar embodiments may be used or modifications and additions may be made to the described embodiments for performing the same function. Furthermore, the various illustrative embodiments may be combined to produce the desired results. Therefore, the methods of mitigating the chemical conversion of α-nootkatol to nootkatene in terpene blend feed, methods of making terpene blends, terpene blends, flavour compositions, fragrance compositions, beverage products, food products and fragrance products should not be limited to any single embodiment, but rather construed in breadth and scope in accordance with the recitation of the appended claims. It will be understood that the embodiments described herein are merely exemplary, and that one skilled in the art may make variations and modifications without departing from the spirit and scope of the invention. All such variations and modifications are intended to be included within the scope of the invention as described herein above. Further, all embodiments disclosed are not necessarily in the alternative, as various embodiments of the invention may be combined to provide the desired result.

The invention claimed is:

1. A method of mitigating or preventing the conversion of nootkatol to nootkatene comprising:
   providing a feed containing nootkatol and at least one compound that catalyzes the conversion of nootkatol to nootkatene; and
   either (i) separating via distillation at least a portion of the nootkatol from the at least one compound that catalyzes the conversion of nootkatol to nootkatene, wherein a base is added to the feed prior to distillation, or (ii) neutralizing at least a portion of the at least one compound that catalyzes the conversion of nootkatol to nootkatene.

2. The method of mitigating or preventing the conversion of nootkatol to nootkatene of claim 1, wherein the feed comprises a blend of volatile terpenes comprising α-nootkatol.

3. The method of mitigating or preventing the conversion of nootkatol to nootkatene of claim 1, wherein the compound that catalyzes the conversion of nootkatol to nootkatene comprises at least one fatty acid.

4. The method of mitigating or preventing the conversion of nootkatol to nootkatene of claim 3, wherein the at least one fatty acid is selected from saturated and unsaturated fatty acids having 2 to 28 carbon atoms.

5. The method of mitigating or preventing the conversion of nootkatol to nootkatene of claim 1, wherein the distillation comprises a one-stage distillation.

6. The method of mitigating or preventing the conversion of nootkatol to nootkatene of claim 1, further comprising carrying out fractional distillation following either (i) or (ii).

7. The method of mitigating or preventing the conversion of nootkatol to nootkatene of claim 1, wherein the base is a nitrogen-containing compound.

8. The method of mitigating or preventing the conversion of nootkatol to nootkatene of claim 7, wherein the nitrogen-containing compound comprises an amine.

9. The method of mitigating or preventing the conversion of nootkatol to nootkatene of claim 8, wherein the amine comprises a tertiary amine.

* * * * *